(12) United States Patent
Lowen et al.

(10) Patent No.: US 6,579,234 B2
(45) Date of Patent: Jun. 17, 2003

(54) ENHANCED DIAGNOSIS OF PSYCHIATRIC DISORDERS WITH HEARTBEAT DATA

(75) Inventors: Steven B. Lowen, Burlington, MA (US); Martin H. Teicher, Waltham, MA (US)

(73) Assignee: The McLean Hospital Corporation, Belmont, MA (US)

( * ) Notice: Subject to any disclaimer, the term of this patent is extended or adjusted under 35 U.S.C. 154(b) by 0 days.

(21) Appl. No.: 10/014,633

(22) Filed: Oct. 26, 2001

(65) Prior Publication Data

US 2002/0151802 A1 Oct. 17, 2002

Related U.S. Application Data

(60) Provisional application No. 60/243,963, filed on Oct. 27, 2000.

(51) Int. Cl.[7] .................................................. A61B 5/00
(52) U.S. Cl. ........................ 600/300; 600/500; 600/509
(58) Field of Search ................................. 600/500, 300, 600/481, 509

(56) References Cited

U.S. PATENT DOCUMENTS

| | | | |
|---|---|---|---|
| 6,245,021 B1 * | 6/2001 | Stampfer | 600/481 |
| 6,260,022 B1 | 7/2001 | Brown | 705/2 |
| 6,334,778 B1 | 1/2002 | Brown | 434/258 |

* cited by examiner

*Primary Examiner*—Robert L. Nasser
(74) *Attorney, Agent, or Firm*—Clark & Elbing LLP

(57) ABSTRACT

The invention provides methods for enhancing the differential diagnosis of attention deficit disorder (ADHD) versus anxiety disorder in a human patient undergoing testing for ADHD.

11 Claims, No Drawings

ENHANCED DIAGNOSIS OF PSYCHIATRIC DISORDERS WITH HEARTBEAT DATA

CROSS REFERENCE TO RELATED APPLICATION

This application claims benefit from United States provisional application, serial number 60/243,963, which was filed Oct. 27, 2000.

BACKGROUND OF THE INVENTION

Through the use of the OPTAx test system, analysis of combined motion and performance data provides an excellent method for distinguishing between normal children and those with attention-deficit and hyperactivity disorder (ADHD). Children with anxiety disorder present with many of the same symptoms as those with ADHD. The OPTAx system, like other computer test systems, has difficulty in making a differential diagnosis between ADHD and anxiety disorder.

SUMMARY OF THE INVENTION

We have invented a method for enhancing the differential diagnosis of ADHD versus anxiety disorder in a human patient undergoing testing for ADHD; the method involves, simultaneously with the conducting of ADHD testing, detecting and analyzing the heartbeat pattern in the subject. Increased sympathetic activity and/or decreased parasympathetic activity indicates a differential diagnosis of anxiety disorder.

The method of the invention allows the differentiation of anxiety disorders and attention-deficit and hyperactivity disorder, which is important so that the subject is not misdiagnosed. Treatment protocols for these conditions are different, and so it is crucial that the subject be accurately diagnosed for his or her specific condition.

DETAILED DESCRIPTION

Anxiety manifests itself in heartbeat patterns, with anxious subjects exhibiting markedly increased sympathetic activity and decreased parasympathetic activity. To aid in the differentiation of ADHD versus anxiety disorder, simultaneously with the conducting of testing for ADHD, the heartbeat pattern of a subject is analyzed. Those subjects which exhibit increased sympathetic activity and/or decreased parasympathetic activity can be flagged for a more cautious interpretation of the ADHD test results.

In a preferred embodiment, testing for ADHD involves measuring movement and response to a visual stimulus of the subject. The heartbeat pattern is detected either with two or more sensors applied to the subject's torso to detect electrical signals emanating from the subject's heart, or by measuring light transmission of a single wavelength through the subject's body. Alternatively, a fluctuation in the ratio of light intensities at two different wavelengths, or ratio of infrared light of two different wavelengths may be measured in order to detect the heartbeat pattern. The light can be infrared light, or light of any other wavelength. The light can be transmitted through'the subject's finger, earlobe, or any other body region.

In addition, high levels of stress can occur in test-phobic subjects or in individuals under inordinate pressure. Such high levels of stress can also interfere with an accurate interpretation of ADHD test results. As stress can be inferred from heartbeat pattern tests in the same manner as anxiety is detected, those subjects experiencing stress also can be differentiated from those with ADHD by analyzing heartbeat patterns.

When the methods of the invention are used, those subjects displaying increased sympathetic activity or decreased parasympathetic activity during the testing for ADHD may be flagged for a more circumspect interpretation of the ADHD test results. These patients may also undergo further tests to confirm the correct diagnosis of ADHD or anxiety.

The system used to differentiate between ADHD and anxiety consists of five connected parts that interface with a main computer that also runs the attentional task and performs initial data analysis. The main computer administers the attentional task, for example, by displaying objects on a video screen, in response to which the subject responds by pressing specific keys on a keyboard. The computer records this information and uses it as part of the assessment of ADHD or anxiety. The five parts of the system that interface with the computer are as follows.

1. Two or more sensors that are applied to the subject's torso to detect electrical signals emanating from the heart. Alternatively, other types of sensors may be used for detecting the heartbeat of the subject. For example, the heartbeat may be detected by measuring the ratio of infrared light of two different wavelengths transmitted through the subject's finger.
2. One or more amplifiers for increasing the strength of the electrical signals from the heart.
3. One or more peak detectors to determine the times of occurrence of R-waves (heartbeat'data). Alternatively, the output signal from the sensors may be amplified and digitized directly, and the peak detection may be performed by a digital signal processing system interface board or by the computer software.
4. An interface unit that conveys the detected peaks to the computer for analysis.
5. A motion detection system, for example, one or more reflective markers placed on the subject, along with an infrared camera interfacing with the computer.

The computer, in addition to including the software required for running the ADHD test, contains software that performs processing (analysis) of the R-wave data. For example, the software may carry out Fourier analysis on the R-wave data, yielding the average power in several frequency bands over the duration of the test. For example, anxiety is associated with an increase in sympathetic activity, and a decrease in parasympathetic activity. An estimate of sympathetic activity is derived from the power in the low frequency (LF, 0.04–0.15 cycles/beat) band of heartbeat data, and parasympathetic from both the LF and high frequency (HF, 0.15–0.4 cycles/beat) bands. The LF/HF ratio, for example, provides an indication of the degree of the subject's level of anxiety. These heartbeat pattern data are correlated with the data from the attentional task test (e.g., key press and movement information) and used to generate a report which aids in the determination of a 'diagnosis of ADHD or anxiety.

Alternatively, the heartbeat data may be analyzed in other ways. For example, wavelet transforms, or other linear or nonlinear filters may be used instead of Fourier analysis. The times between R-waves may be used directly for report generation, rather than computing the power over various frequency bands. In addition, the average times of the occurrence of R-waves may be averaged over the entire duration of the test, or may be broken down into several smaller averaging times.

Furthermore, in an alternative to the software that performs the preliminary processing of the R-wave data, a specialized digital signal processing interface board which performs some or all of the preliminary data processing may be used.

One example of a system that provides diagnostic information for assessing the degree or presence of ADHD in subjects is the OPTAx system, described, for example, by Teicher et al. (J. Am. Acad. Child Adolesc. Psychiatry 35: 334–342, 1996), incorporated herein by reference. This system includes a computer with a video screen and keyboard, an infrared camera and associated electronics, one or more infrared reflective markers placed on the subject, and a connection to the Internet, either through a direct link or through a telephone line via an Internet service provider. Shapes are displayed on the video screen, for which different responses are required of the subject. For example, the subject is instructed to press the space bar on the keyboard if an eight-pointed star is displayed at any position on the video screen, and to do nothing when a five pointed star appears on the screen. Whether the subject presses a key, as well the time it takes for the key to be pressed, are recorded and stored. In addition, the infrared camera determines the subject's movements throughout the test, by detecting the infrared reflective markers placed on the subject. At the end of the test, the recorded data (key press and movement information) are transmitted over the Internet connection to a central processing station, where a report is generated and transmitted back to the testing site.

What is claimed is:

1. A method for enhancing the differential diagnosis of attention deficit disorder (ADHD) versus anxiety disorder in a human subject undergoing testing for ADHD, said method comprising, simultaneously with the conducting of said ADHD testing, detecting and analyzing the heartbeat pattern in said subject, wherein increased sympathetic activity and/or decreased parasympathetic activity indicates a differential diagnosis of anxiety disorder.

2. The method of claim 1, wherein said testing for ADHD comprises measuring the movement and response to a visual stimulus of said subject.

3. The method of claim 1, wherein said heartbeat pattern is detected using two or more sensors applied to said subject's torso to detect electrical signals emanating from said subject's heart.

4. The method of claim 1, wherein said heartbeat pattern is detected by measuring light transmission through said subject's body.

5. The method of claim 4, wherein said light is infrared light.

6. The method of claim 4, wherein said light is a wavelength of light other than infrared light.

7. The method of claim 4, wherein said measuring is of a fluctuation in the light intensity at a single wavelength.

8. The method of claim 4, wherein said measuring is of a fluctuation in the ratio of light intensities at two different wavelengths.

9. The method of claim 5, wherein said measuring is of the ratio of infrared light of two different wavelengths.

10. The method of claim 4, wherein said light is transmitted through said subject's finger.

11. The method of claim 4, wherein said light is transmitted through said subject's earlobe.

* * * * *